United States Patent [19]
Mantovanini et al.

[11] Patent Number: 5,750,536
[45] Date of Patent: May 12, 1998

[54] TROPYL 7-AZAINDOL-3-YLCARBOXYAMIDES AS ANTITUSSIVE AGENT

[75] Inventors: Marco Mantovanini; Gabriella Melillo; Luisa Daffonchio, all of Milan, Italy

[73] Assignee: DOMPE ' SpA, L'Aquila, Italy

[21] Appl. No.: 615,173
[22] PCT Filed: Aug. 4, 1994
[86] PCT No.: PCT/IB94/00234
  § 371 Date: Apr. 2, 1996
  § 102(e) Date: Apr. 2, 1996
[87] PCT Pub. No.: WO95/04742
  PCT Pub. Date: Feb. 16, 1995

[30] Foreign Application Priority Data
Aug. 5, 1993 [IT] Italy .................. MI93A1780

[51] Int. Cl.$^6$ ............... A01N 43/42; C07D 471/02; C07D 209/02
[52] U.S. Cl. ............... 514/300; 546/113; 548/467
[58] Field of Search ............... 546/113; 548/467; 514/300

[56] References Cited

FOREIGN PATENT DOCUMENTS

| 0 504 679 | 9/1992 | European Pat. Off. . |
| 0 581 165 | 2/1994 | European Pat. Off. . |
| 4-21681   | 1/1992 | Japan . |

OTHER PUBLICATIONS

Kato et al., "Preparation of Pyrrolopyridine ...", Chemical Abstracts, vol. 116 (1992), p. 778, ABS #255499a.
Caplus Abstract of JP 4-21681, (1992).

M. Kato et al—preparation of pyrrolopyridine derivatives as 5-hydroxytryptamine (5-HT) antagonist—Chemical Abstracts—vol. 116, 1992.

Primary Examiner—Mukund J. Shah
Assistant Examiner—Tamthom T. Ngo
Attorney, Agent, or Firm—Armstrong, Westerman, Hattori, McLeland & Naughton

[57] ABSTRACT

Tropyl 7-azaindol-3-ylcarboxamides of the formula

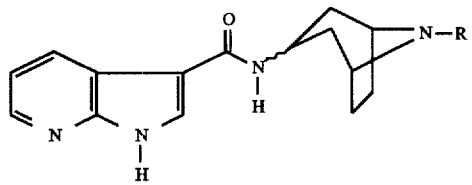

or their N-oxides of the formula

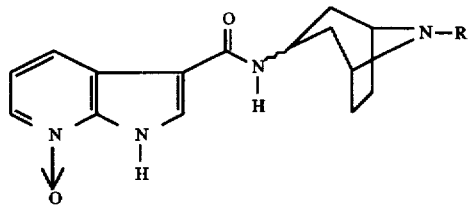

wherein R is hydrogen, alkyl, cyclo-alkyl, arylalkyl or acyl, are particularly effective as antitussive agents.

5 Claims, No Drawings

TROPYL 7-AZAINDOL-3-YLCARBOXYAMIDES AS ANTITUSSIVE AGENT

This is a 3H application of PCT/IB 94/00234 filed on Aug. 4, 1994.

The present invention refers to tropyl 7-azaindol-3-ylcarboxyamides of formula (I)

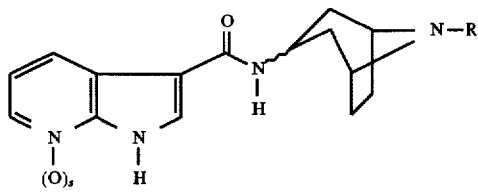

wherein the symbol ⌇
indicates that compounds (I) may have the configuration exo(or β-) or endo(or α-) and R represents a hydrogen atom; a saturated linear or branched $C_1$–$C_4$ alkyl; a $C_7$–$C_9$ arylalkyl; a —$(CH_2)_n$—$(C_3$–$C_7)$ cycloalkyl group wherein n is an number between 0 and 4; a $C_1$–$C_{12}$ acyl group, s repreents 0 or 1.

As $C_3$–$C_7$ membered cycloaliphatic ring cyclopropyl, cyclopentyl and cyclohexyl are preferred.

As $C_7$–$C_9$ arylalkyl the benzyl and the phenethyl radical are preferred.

As —$(CH_2)$n—$(C_3$–$C_7)$ cycloalkyl group, the cyclopropylmethyl group is preferred.

As $C_1$–$C_{12}$ acyl group the formyl group is preferred.

Among $C_1$–$C_4$ alkyl radicals are preferred the methyl, ethyl and isopropyl radicals.

A further object of the invention is represented by the compounds of formula (I) wherein the aminotropyl group is protected by a suitable conventional protecting group among which is preferred the ter-butoxycarbonyl. Also included in the scope of the invention are the acid addition salts of the compounds (I) with suitable, non-toxic, pharmaceutically acceptable acids. Among these salts are cited the hydrochorides, hydrobromides, alkyl and arylsulfonates, succinates, tartrates and citrates.

The compounds of formula (I) are obtained by reaction of a tropylamine of formula (III):

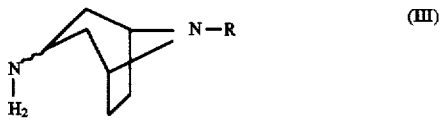

wherein the symbols R and ⌇
have the above defined meaning, with an optionally activated azaindolyl-3-carboxylic acid (IV):

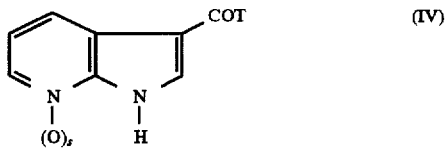

wherein the symbol s, has the above mentioned meaning and T represents a hydroxy group or the residue of a carboxylic acid activating group. Preferred activating groups are those well known in the art such as, for example, chorine, bromine, azide, imidazolide, p-nitrophenoxy, 1-benzotriazole, N—O-succinimide, acyloxy and more specifically, pivaloyloxy, C1–C4 alkoxycarbonyloxy, such as, for example, $C_2H_5OCO$—O—, a dialkyl- or a dicycloalkyl-O-ureide. The carboxyamides of formula (I) are isolated from the reaction mixture as free bases or as addition compounds with a suitable mineral or organic acid. When the compounds of formula (IV) are used in their free acid form, the reaction is carried out in the presence of a condensing agent such as, for example, a carbodiimide, optionally in the presence of an activating agent such as, for example, hydroxybenzotriazole or hydroxysuccinimide, with the intermediate formation of dialkyl- or dicycloalkyl-O-ureides. Typical condensing agents are the dicyclohexyl- and the diisopropylcarbodiimide, carbodiimides soluble in an aqueous medium etc. Preferred reaction conditions are those which provide the use of equimolar amounts of the reagents, in inert solvents such as ethyl acetate, aromatic hydrocarbons such as benzene and toluene, cycloalkanes such as cyclohexane, dioxane, tetrahydrofuran, dimethylsulfoxide, dimethylformamide, N-methylpyrrolidone, acetonitrile and the mixtures thereof, operating at a temperature between room temperature and the reflux temperature of the mixture, preferably at 50°–60° C.

The bicyclic tropylamines (III) are generally well known and also commercially available compounds. They may be prepared using methods known in the art; see for example, the method for the preparation of 3α-tropylamine of S. Archer et al., J. Amer. Chem. Soc., 79, 4194, 1957 and the method described for the preparation of 3β-tropylamine R. Willstätter et al., Chem. Ber., 31, 1201, 1898, S. Archer et al., J. Amer. Chem. Soc., 80, 4677, 1858, and also A. Stoll et al., Helv. Chim. Acta 38, 559, 1955; further preparations of said tropylamines are described by P. Dostert et al., FR 2.449.570 (13 Aug. 1982) C.A. 98, 126444q (1983); P. Donatsch et al., DE 33 22754 (29 Dec. 1983); M. Langlois et al., FR 2.548.666 (11 Jan. 1985) C.A. 103, 123757e (1985); E. A. Watts PCT WO 85 00.170 (17 Jan. 1985) C.A. 103 123376e (1985); D. Lednicer et al., EP 147.044 (3 Jul. 1985) C.A. 104 1949 1986.

The preparation of the 1H-pyrrole[2,3-b]pyridine-3-carboxylic acid 7-oxide, as well as a general procedure for the preparation of 1H-pyrrole[2,3-b]pyridine 7-oxide, has been described by S. W. Schneller et al., (J. Org. Chem., 45, 4045, 1980).

The preparation of the 1H-pyrrole[2,3-b] pyridine-3-carboxylic acid as well as the ethyl ester thereof have been described by M. M. and B. L. Robinson on J. Amer. Chem. Soc., 78, 1247, 1956. In general, 7-azaindoles and their homologues 1- or 2-substituted or 1- or 2-disubstituted, for the preparation of which see for example, R. R. Lorenz et al., J. Org. Chem., 30, 2531, 1965 and references cited therein, may be converted by a Mannich reaction into their corresponding 3-dialkylaminomethyl derivatives and then transformed in the corresponding 3-formyl-7-azaindoles which, substantially according to the above mentioned procedure of M. M. and B. L. Robinson, are converted into their corresponding esters and carboxilic acids.

More particularly it has been found that, in a halogenated solvent and in the presence of a suitable catalyst such as aluminum chloride, i.e. in Friedel-Krafts conditions, the 7-azaindoles themselves react with a trihaloacetylhalides, preferably tricloacetylchloride, to give, with a yield almost quantitative, the corresponding 3-trihaloacetyl-7-azaindoles such as, for example, 3-trichloroacetyl-1H-pyrrole[2,3-b] pyridine which, with further treatment with bases, such as potassium hydroxide, undergo the haloformic transposition into the corresponding 7-azaindolyl-3-carboxylic acids.

The following Examples are given by way of better illustrating the invention without limiting it.

EXAMPLE 1

N-(endo-8-methyl-8-azabicyclo[3.2.1]oct-3-yl)-7-azaindolyl-3-carboxamide (Compound A)

In an inert gas atmosphere and under stirring, a solution of 5.4 ml of trichloroacetyl chloride in 27 ml dichloromethane is added in the course of 10 minutes to a suspension of 6.8 g aluminum chloride in 54 ml dichloromethane cooled to −78° C. It is maintained at this temperature for 15 minutes then warmed up to −40° C., maintaining under stirring for a further 45 minutes. A solution of 2 g 7-azaindole in 10 ml dichloromethane is then added, stirred for 15 minutes at −40° C. and the temperature is allowed to rise to 0° C. and stirring continued for a further hour. Milliliters 26 of an aqueous solution of 1H hydrochloric acid are added carefully maintaining the temperature between 0° and 15° C.; after decomposition of the reagents, the phases are separated and the organic phase is washed with water and treated under strong stirring with sodium bicarbonate heptahydrate to obtain a white crystalline solid which is filtered and it gives 2.6 g 3-trichloroacetyl-1H-pyrrole-[2,3-b]pyridine melting at 260° C. (with decomposition). The so obtained compound is suspended in 15 ml of a 10% potassium hydroxide aqueous solution and the suspension is kept under strong stirring until complete dissolution. By acidification of the solution to pH 3–4 with a 37% hydrochloric acid aqueous solution, 1.5 g 7-azaindolyl-3-carboxylic acid separate by precipitation, melting point 230°–240° C. (with decomposition).

To a solution of 1.5 g 7-azaindolyl-3-carboxylic acid in 24 ml of a mixture 1:1 of tetrahydrofuran:dimethylformamide, 1.29 g endo-8-methyl-8-aza-bicyclo[3.2.1]oct-3-ylamine and 2.1 g dicyclohexylcarbodiimide are added.

The mixture is heated for 3 hours at 50° C., then it is evaporated to small volume, acidified with 2N hydrochloric acid and filtered removing the dicyclohexylurea precipitate. The filtrate is saturated with sodium chloride and after being made alkaline to pH 11 with sodium hydroxide, it is extracted with chloroform and it gives, by evaporation of the solvent and crystallization of the residue from ethyl ether, 1.24 g N-(endo-8-methyl-8-azabicyclo[3.2.1]oct-3-yl)-7-azaindolyl-3-carboxamide melting at 273° C. (Compound A). Operation is carried out according to the previously described procedure and using instead of endo-8-methyl-8-azabicyclo [3.2.1]oct-3-ylamine, 1-azabicyclo[2.2.2]oct-3-yl-amine, N-(1-azabicyclo[2.2.2]oct-3-yl)-7-azaindolyl-3-carboxamide melting at 275°–280° C. is obtained (Compound B).

EXAMPLE 2

N-(8-methyl-8-azabicyclo[3.2.1]oct-3α-yl)-7-azaindolyl-3-carboxamide 7-oxide.

To a solution of 1.5 g 7-azaindolyl-3-carboxilic acid 7-oxide in 30 ml acetonitrile, 2 g of 1-(3-dimethylaminopropyl)-3-ethylcarbodiimide hydrochloride are added in portions.

After 15 minutes of stirring, a solution of 1.29 g 3α-tropylamine in 10 ml of acetonitrile is added. It is kept at room temperature for 2 hours, heated to 50° C. for 2 hours, concentrated under vacuo to a third of its volume and diluted with 100 ml of water. After several extractions with ethyl acetate, the organic phases are collected together and evaporated to dryness. The residue is purified by chromatography over silica gel (CHCl$_3$:MeOH) to give 1.12 g N-(8-methyl-8-azabicyclo[3.2.1]oct-3α-yl)-7-azaindolyl-3-carboxamide 7-oxide.

EXAMPLE 3

N-(8-cyclopropylmethyl-8-aza-bicyclo[3.2.1]oct-3β-yl)-7-azaindolyl-3-carboxamide.

A solution of 2.9 g N-hydroxysuccinimide in 10 ml tetrahydrofuran is added to a solution of 1.84 g 7-azaindolyl-3-carboxylic acid in 30 ml of a 1:1 tetrahydrofuran and dimethylformamide mixture cooled to 0° C. and under stirring. A solution of 2.1 ml morpholynethylisonitrile in 10 tetrahydrofuran ml is dripped therein and stirring is maintained for a further two hours to room temperature. It is diluted with 5 volumes of water, tetrahydrofuran is removed by evaporation under vacuum, it is acidified to pH 3–4 with a potassium acid sulphate aqueous solution and extracted with ethyl acetate. From the collected together organic extracts, by evaporation of the solvent, 2.6 g 7-azaindolyl-3-carboxylic acid succinimide ester crystallizes.

Grams 1.02 of the so obtained succinimide ester are dissolved at room temperature and in argon atmosphere in 7.5 ml acetonitrile and to the solution 5 ml of a solution of 0.75 g 3β-amino-8-cyclopropylmethyl-8-azabicyclo[3.2.1] octane in 0.5 ml acetonitrile are added. After 8 hours, the mixture is concentrated under vacuum to small volume and diluted with a sodium bicarbonate saturated solution until a slight alkaline pH. It is extracted four times with 20 ml each of ethyl acetate and from the collected together extracts, after evaporation of the solvent and crystallization from ethyl ether, 1.5 g of N-(8-cyclopropylmethyl-9-aza-bicyclo [3.2.1]oct-3βyl)-7-aza-indolyl-3-carboxiamide are obtained.

In a similar manner by reaction with the suitable 3-amino-8-azabicyclo[3.2.1] octane are obtained:

N-(8-cyclopropylmethyl-8-azabicyclo[3.2.1]oct-3α-yl-7-azaindolyl-3-carboxyamide;

N-(8-formyl-8-azabicyclo[3.2.1]oct-3α-yl)-7-azaindolyl-3-carboxyamide;

N-(8-tert-butoxycarbonyl-8-azabicyclo[3.2.1]oct-3α-yl)-7-azaindolyl-3-carboxyamide;

N-(8-phenylethyl-8-azabicyclo[3.2.1]oct-3α-yl)-7-azaindolyl-3-carboxyamide;

N-(8-benzyl-8-azabicyclo[3.2.1]oct-3α-yl)-7-azaindolyl-3-carboxyamide;

N-(8-cyclohexylmethyl-8-azabicyclo[3.2.1]oct-3α-yl)-7-azaindolyl-3-carboxyamide;

N-(8-cyclopentylmethyl-8-azabicyclo[3.2.1]oct-3α-yl)-7-azaindolyl-3-carboxyamide;

N-(8-ethyl-8-azabicyclo[3.2.1]oct-3α-yl)-7-azaindolyl-3carboxyamide;

N-(8-isopropyl-8-azabicyclo[3.2.1]oct-3α-yl)-7-azaindolyl-3-carboxyamide.

EXAMPLE 4

N-(8-azabicyclo[3.2.1]oct-3α-yl)-7-azaindolyl-3-carboxyamide tri-fluoroacetate.

A solution of 0.3 g N-(8-tert-butoxycarbonyl-8-azabicyclo[3.2.1] oct-3α-yl-7-azaindolyl-3-carboxyamide in 2 ml of dichloromethane and 2 ml of trifluoroacetic acid is maintained for 8hours at room temperature then the reaction mixture is evaporated to dryness under vacuum and the residue, crystallized from ethyl ether:hexane, and it gives the trifluoro acetate of N-(8-azabicyclo[3.2.1]oct-3α-yl)-7-azaindolyl-3-carboxyamide.

Benzoyl N-quinuclidinylamides and N-tropylamides and analogous amides of aryl- and heteroarylcarboxylic acids represent compounds which in the last decade were the object of wide researches having as aim the identification and the functional characterization of the subtypes of the serotonin (5-HT) receptor and the realization of ligands having high bond affinity and high receptor specificity. Substances belonging to the same family of compounds have resulted clinically effective in the control of the emesys induced by antitumoral chemotherapy, a pharmacological event which was suppose to be modulated by 5-HT$_3$ receptors in the area postrema. Lastly there are pharmacological indications which make believe that these substances because they are 5-HT$_3$ antagonists, may be useful in correcting affections of the central nervous system, such as, for example, schizophrenia, anxiety or the loss of memory, since 5-HT$_3$ receptors also seem to modulate the cholinergic neurons.

Specific examples of 5-HT$_3$ antagonists are, for example, Ondasetron, BRL 24682 or N-(endo-8-methyl-8-azabicyclo-[3.2.1]oct-3-yl)-2-methoxy-4-amino-5-chlorobenzamide, ICS-205-930 or (endo-8-methyl-8-azabicyclo[3.2.1]oct-3-yl)indolyl-3-carboxylate.

More recently, both quinuclidyl- and tropyl-amides of the 7-methyl- 8-azaindolyl-3-carboxylic acid (T. Higashino et al., Toyo Jozo Co., EP 483 836 (06 May 1992), C.A. 117 171436K and 2-methylimidazol[1,2-a]pyridin-3-carboxylic acid (K. Nitta et al., Mitsubishi Kasei Corp. JP 01258679 (16 Oct. 1989), C.A. 112 178986v) have been described as 5-HT$_3$ antagonists and therefore are useful as antiemetic, in the prevention of nausea by cis-Platin and, more in general, as antiserotoninergic drugs to be used for the treatment of the migraine and anxiety.

The amides of the 7-azaindol-3-carboxylic acid (F. D. King, Beecham Group, EP 254 584 (27 Jan. 1988) C.A. 109 93018u) have also been described as 5-HT$_3$ -antagonists. Lastly, more recently, M. Kato et al. (Fujisawa Pharmac., JP 04021681 (24 Jan. 1991) C.A. 116 255499a) describe pyrrolpyridinecarboxyamides of azabicycloalkylamines as typical 5-HT$_3$ antagonists with particular mention to the amides of 3-amino-8-methylazabicyclo[3.2.1]octane with 1-methyl and 1-ethyl-7-azaindolyl-3-carboxylic acids.

Compounds A and Compounds B of the present invention, which are examples of endo-tropyl and quinuclidylamide of 7-azaindolyl-3-carboxylic acid respectively have been studied "in vitro" for their interaction with the 5-HT$_1$, 5-HT$_2$ and 5-HT$_3$ receptors.

TABLE I

| Binding Test: | 5-HT$_1$ | 5-HT$_2$ | 5-HT$_3$ |
|---|---|---|---|
| | % of inhibition at 3.6 10$^{-5}$M | | IC$_{50}$M |
| Ondasetron | 7.6 | 21.7 | 3 10$^{-9}$ |
| Compound A (7-azaindolylcarboxy tropylamide) | 0.0 | 8.6 | 3 10$^{-6}$ |
| Compound B (7-azaindolylcarboxy quinuclidylamide) | 37.0 | 3.9 | 3 10$^{-7}$ |

From the above study a first indication of an atypic behaviour of 7-azaindolyl-3-carboxylic acid tropylamides when compared to the corresponding quinuclidylamid surprisingly appeared.

The interaction of Compounds A and B with other receptors ($\alpha_1$, $\alpha_2$, benzodiazepine (o bzd), GABA A, $\delta$) in comparison to the typical 5-HT$_3$ antagonist Ondastron and BRL 24682 has been studied and for each case the displacement % of the single selective ligand from the corresponding receptor at concentration 10$^{-5}$M of the compounds under examination, has been evaluated.

TABLE II

| | Dispacement percentage | | | | |
|---|---|---|---|---|---|
| Receptors: | $\alpha_1$ | $\alpha_2$ | bdz | Gaba A | $\sigma$ |
| Ondasetron | 72 | 30 | * | 38 | 45 |
| BRL 24682 | 28 | 16 | 98 | 89 | 0 |
| Compound A | 13 | * | * | 83 | 70 |
| Compound B | 7 | * | * | 6.7 | 26 |

*not active: no capacity of displacement of the ligand at a conc. 10$^{-5}$M.

The disparity in behaviour between 7-azaindolyl-3-carboxylic acid quinuclidyl- and tropyl-amides results even more evident from the above-listed data. 7-Azaindolylcarboxamide (Compound A) shows a very weak interaction with 5-HT$_3$ receptors: 1,000 times lower than that of Ondasetron, which is a typical 5-HT$_3$ antagonist, and logarithmically lower than that of Compound B.

Compound A itself shows surprisingly an unusual ability of a double interaction, apparently selective, towards GABA A and $\delta$ receptors, which ability is definitely weak or absent in the corresponding quinuclidylamide and, to the contrary, it seems aspecific in 5-HT$_3$ antagonist Ondasetron.

As to the other 5-HT$_3$ antagonist, BRL 24682, it is evident its high interaction with the benzodiazepine and GABA A receptors, and its complete lacking of interaction with the $\sigma$ receptors, thus allowing to exclude that the selective interaction of 7-azaindolylcarboxytropylamide (Compound A) with GABA A and $\delta$ receptors be a characteristic generally present in potential 5-HT$_3$ antagonists, or, at least in substances so defined on the bases of a simple chemical structure analogy.

Besides these differences "in vitro" on the receptor behaviour great differences has been evidenced "in vivo" in the tussive stimulus inhibition provoked by inhalation of irritant citric acid as well as capsaicine aqueous solutions.

The compounds have been tested in guinea pigs in comparison to codeine, used as standard compound, at the single dose of 100 mg/kg according to the technique of Charlier et al., (Arch. Int. Pharmacodyn., 134, 306, 1961) which has been slightly modified.

The percent reduction evaluated in the number of short coughs after administration of the compound under examination taken in comparison to the number of short coughs observed in each of the animals to which the compound was administered, have been noted.

For each of the compounds under examination it has been also tested the effect on the increase of the sleeping time induced by barbiturates. The test was carried out on mice by oral administration of a single dose of 100 mg/kg of the compound.

The data obtained are listed in the following Table III.

TABLE III

| | % INHIBITION of the coughing stimulus by: | | |
|---|---|---|---|
| | ac. citric | capsaicin | sleeping time increase |
| Ondasetron | 30.5 | 50.5 | −8* |
| BRL 24682 | 44.1 | n.d. | +34.8 |

TABLE III-continued

| | % INHIBITION of the coughing stimulus by: | | |
|---|---|---|---|
| | ac. citric | capsaicin | sleeping time increase |
| Compound A (7-azaindolylcarboxy tropylamide) | 61.7 | 76.30 | −28.9 |
| Compound B (7-azaindolylcarboxy quinuclidylamide) | 46.0 | 21.0 | −7 |
| Codeine | 63.2 | 58.4 | +106.4 |

*at the dose of 10 mg/kg    n.d.: not determinable

In a successive study, carried out at different doses, using as comparison compounds typical antitussive compounds commonly used in therapy, either having a central effect, i.e. codeine, or having a peripheral effect, i.e. levodropropizine, it has been observed that the protecting antitussive effect of 7-azaindolylcarboxytropylamine (Compound A) depends on the dose administered. For these compounds as well as for the most interesting reference compounds the dose inhibiting 50% of the short coughs ($ID_{50}$) induced either by citric acid or capsaicine has been determined.

TABLE IV

| | $ID_{50}$ in mg/kg os (95% confidence) Coughing stimulus | | |
|---|---|---|---|
| | Ac. citric | Capsaicin | 2N $H_2SO_4$ |
| Levodropropyzina | 151 (126–180) | 145 (84–252) | 265 (168–240) |
| Codein | 65 (57–74) | 74 (52)107) | 102 (55–190) |
| Ondasetron | 209 (126–349) | 97 (36–261) | — |
| Compound A | 57 (41–80.5) | 51 (33–77) | — |

— not tested

In both pharmacological tests only 7-azaindolyl-3-carboxy-endo-N-tropylamide (Compound A) showed to be effective. Compound A proved to be at least equiactive as codeine, and advantageously in respect to the latter, it does not show any increase of the sleeping time induced by barbiturates.

It is assumed that Capsaicine releases substance P from the peripheral nerve endings of the sensitive fibers C and determines the necrosis of the same. It is known that capsaicine administration provokes the formation of an exudate (extra vasation by capsaicine) which can be evaluated by concomitant Evans bleu administration.

Solely Compound A and not Ondasetron has been found to give a 42% protection (in comparison with non-treated animals) from capsaicine extravasation when the compounds are administered at 10 mg/kg dosage by intraperitoneal route. A similar protection has been observed after cis-2-benzhydryl-1-azabicyclo-[2.2.2]octane-3-(2-methoxybenzyl amine (CP 96 345, a non-peptide antagonist of substance P) administration at 10 mg/kg i.p. It is worth to underline that the same substance CP 96 345 has been found to protect guinea pigs from cough induced by capsaicin being a 26 and 42% short cough inhibition evaluated after intraperitoneal administration of 10 and 40 mg/kg respectively.

Further compound A (N-endo-8-methyl-8-azabicyclo [3.2.1] oct-3-yl)-7-azaindolyl-3-carboxamide has been tested for its antitussive effect in comparison to the closest compound belonging to the class of compounds of Japanese Kokai Tokkyo Koho JP 04 21 681, i.e., 8-methyl-8-azabicyclo [3.2.1] oct-3-yl)-1-methyl-7-azaindolyl-3-carboxamide. The compounds were administered by os at a single dose of 100 mg/kg on mice using as irritant agent capsaicine aqueous solution according to the previous mentioned technique.

TABLE V

| Compound | n° short coughs | average n° ± s.e. | inhib. % |
|---|---|---|---|
| Control | 8 6 5 8 7 9 | 7.2 ± 0.6 | — |
| 7-azaindol-ylcarboxy tropylamide | 3 3 0 1 3 1 | 1.8 ± 0.5 | 75% |
| 1-methyl 7-aza-indolylcarboxy tropylamide | 9 5 8 8 6 5 | 6.5 ± 0.7 | 6% |

From the data listed in table V, it is evident compound A is effective as an antitussive compound; while the corresponding methyl derivatives disclosed in JP 04 21 681 were practically ineffective.

Further compound A (N-endo-8-methyl-8-azabicyclo [3.2. 1] oct-3-yl)-7-azaindolyl-3-carboxamide has been tested for its antitussiv effect in comparison to the closest compound belonging to the class of compounds of Jpn. Kokai Tokkyo Koho JP 04 21 681, i.e. 8-methyl-8-azabicliclo [3.2.1] oct-3-yl)-1-methyl-7-azaindolyl-3-carboxamide. The compounds were administered by os at a single dose of 100 mg/kg on mice using as irritant agent capsaicine aqueous solution according to the previous mentioned technique.

TABLE V

| Compound | n° short coughs | average n° ± s.e. | inhib. % |
|---|---|---|---|
| Control | 8 6 5 8 7 9 | 7.2 ± 0.6 | — |
| 7-azaindol-ylcarboxy tropylamide | 3 3 0 1 3 1 | 1.8 ± 0.5 | 75% |
| 1-methyl 7-aza-indolylcarboxy tropylamide | 9 5 8 8 6 5 | 6.5 ± 0.7 | 6% |

From the data listed in table V it is evident the effectiveness of compound A as antitussive compound while the corresponding methyl derivatives disclosed in JP 04 21 681 showed practically to be ineffective.

The compounds of the invention can be then therapeutically employed as antitussive agents without the limitation of the opiate ligand antitussive drugs like as codeine. They are useful in the treatment of coughs of different origin particularly against tussive manifestations mediated by substance P.

More particularly the compounds of the present invention are helpful to prevent nocturnal cough stimuli, due to the administration of ACE-inhibitors, widely used in the hypertension treatments of which conditions the nocturnal cough represents a side effect which is hard to cure.

The compounds of the invention are also useful in the treatment of inflammatory conditions and more generally of those pathological conditions in which substance P and other neuropeptides have a conclusive etiological part and moreover in asthmatic conditions and pain of neurological origin.

The compounds of the invention may be administered by oral, sublingual, endovenous, subcutaneous, intramuscular, rectal route and by inhalation. The preferred doses vary from about 0.05 to about 15 mg/kg/die, depending on the conditions, weight, age of the patient and on the administration route. Higher dosages of the compounds of the invention, even for a prolonged period of time, have no contraindication because of their very low toxicity. Compound A $LD_{50}$ in mice is 1 g/kg by oral route.

The compounds of the invention may be therapeutically used in most of the pharmaceutical preparations, using conventional techniques and excipients as are described in "Remington's Pharmaceutical Sciences Handbook" Hack Publ. Co. New York. USA.

These compositions include capsules, tablets, drinkable solutions, suppositories, vials for parenteral route and by inhalation, systems with controlled release and similar.

We claim:

1. Tropyl 7-azaindol-3-ylcarboxyamide compound of the formula

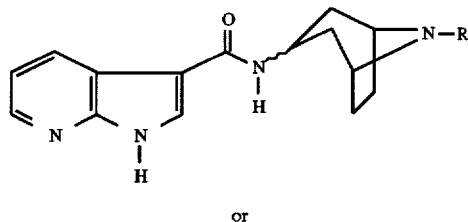

or

-continued

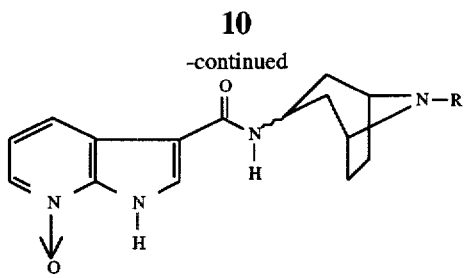

wherein the symbol ～
indicates that the compounds may have an exo or an endo configuration; and R represents hydrogen, a saturated linear or branched $C_1$–$C_4$ alkyl, $C_7$–$C_9$ arylalkyl or $(CH_2)n$—$(C_3$–$C_7)$ cycloalkyl group wherein n is an number between 0 and 4, or a $C_1$–$C_{12}$ acyl group;

or non-toxic pharmaceutically acceptable acid addition salts thereof.

2. A compound according to claim 1, which is N-(endo-8-methyl-8-azabicyclo[3.2.1]oct-3-yl)-7-azaindolyl-3-carboxamide.

3. An antitussive composition comprising a therapeutically effective quantity of a compound according to claim 1 or 2 in combination with a pharmaceutically acceptable carrier.

4. An anti-asthmatic composition comprising a therapeutically effective quantity of a compound according to claim 1 or 2 in combination with a pharmaceutically acceptable carrier.

5. An anti-neurological-origin algesia composition comprising a therapeutically effective quantity of a compound according to claim 1 or 2 in combination with a pharmaceutically acceptable carrier.

* * * * *

UNITED STATES PATENT AND TRADEMARK OFFICE
CERTIFICATE OF CORRECTION

PATENT NO. : 5,750,536
DATED : May 12, 1998
INVENTOR(S) : Marco MANTOVANINI, Gabriella MELILLO, and Luisa DAFFONCHIO It is certified that error appears in the above-identified patent and that said Letters Patent is hereby corrected as shown below:

At column 1, line 24, please delete "repreents" and insert -- represents --.

At column 4, lines 29 and 30, please delete "N-(8-cyclopropylmethyl-9-aza-bicyclo[3.2.1]oct-38yl)-7-aza-indolyl-3-carboxiamide" and insert -- N-(8-cyclopropylmethyl-8-aza-bicyclo[3.2.1]oct-3ß-yl)-7-aza-indolyl-3-carboxiamide --.

At column 8, please delete text spanning lines 25-49.

Signed and Sealed this

Thirteenth Day of October 1998

*Attest:*

BRUCE LEHMAN

*Attesting Officer*  Commissioner of Patents and Trademarks